(12) United States Patent
Watanabe et al.

(10) Patent No.: US 12,196,734 B2
(45) Date of Patent: Jan. 14, 2025

(54) COOKING OIL DEGRADATION DEGREE DETERMINING DEVICE, COOKING OIL DEGRADATION DEGREE DETERMINATION PROCESSING DEVICE, COOKING OIL DEGRADATION DEGREE DETERMINATION METHOD, AND FRYER

(71) Applicant: J-OIL MILLS, Inc., Tokyo (JP)

(72) Inventors: Ryohei Watanabe, Tokyo (JP); Kenichi Kakimoto, Tokyo (JP); Masami Inoue, Tokyo (JP)

(73) Assignee: J-OIL MILLS, Inc., Tokyo (JP)

( * ) Notice: Subject to any disclaimer, the term of this patent is extended or adjusted under 35 U.S.C. 154(b) by 63 days.

(21) Appl. No.: 18/044,396

(22) PCT Filed: Nov. 11, 2021

(86) PCT No.: PCT/JP2021/041579
§ 371 (c)(1),
(2) Date: Mar. 8, 2023

(87) PCT Pub. No.: WO2022/113755
PCT Pub. Date: Jun. 2, 2022

(65) Prior Publication Data
US 2023/0333076 A1    Oct. 19, 2023

(30) Foreign Application Priority Data
Nov. 25, 2020 (JP) ................. 2020-195271

(51) Int. Cl.
*G01N 33/03* (2006.01)
*A23L 5/10* (2016.01)
*A47J 37/12* (2006.01)

(52) U.S. Cl.
CPC ............... *G01N 33/03* (2013.01); *A23L 5/11* (2016.08); *A47J 37/1266* (2013.01)

(58) Field of Classification Search
None
See application file for complete search history.

(56) References Cited

U.S. PATENT DOCUMENTS

| 6,274,850 B1 | 8/2001 | Mercer | |
|---|---|---|---|
| 2011/0084708 A1* | 4/2011 | Yu | G01N 33/03 |
| | | | 73/864.72 |

FOREIGN PATENT DOCUMENTS

| JP | H08182624 | 7/1996 |
|---|---|---|
| JP | 2006226735 | 8/2006 |

(Continued)

*Primary Examiner* — Farhana A Hoque
(74) *Attorney, Agent, or Firm* — Erik J. Overberger; RANKIN, HILL & CLARK LLP (57) ABSTRACT

Provided is a cooking oil degradation degree determination device, etc., capable of accurately determining the degradation degree of fry oil, comprising: a fryer 2 that includes an oil vat 21 for storing frying oil Y therein and a color sample 23 for displaying gradual change in the color of the frying oil Y; a video camera 42 that captures an oil surface image of the frying oil Y; and a controller 5 that executes degradation degree determination processing of the frying oil Y, wherein the color sample 23 is arranged at a position included within an angle of view of the video camera 42 which is the same as an angle of view thereof for the oil surface image, and the controller 5 compares the color of the frying oil Y with colors displayed on the color sample 23, respectively, to determine the degradation degree of the frying oil Y.

7 Claims, 8 Drawing Sheets

(56) References Cited

FOREIGN PATENT DOCUMENTS

| | | |
|---|---|---|
| JP | 2016161301 | 9/2016 |
| JP | 2017049030 | 3/2017 |
| JP | 2017201251 | 11/2017 |
| JP | 2017207460 | 11/2017 |
| JP | 2020038207 | 3/2020 |
| WO | WO2018012431 | 4/2019 |

* cited by examiner

COOKING OIL DEGRADATION DEGREE DETERMINING DEVICE, COOKING OIL DEGRADATION DEGREE DETERMINATION PROCESSING DEVICE, COOKING OIL DEGRADATION DEGREE DETERMINATION METHOD, AND FRYER

TECHNICAL FIELD

The present invention relates to a cooking oil degradation degree determination device, a cooking oil degradation degree determination processing device, a cooking oil degradation degree determination method, and a fryer, which are for determining the degradation degree of cooking oil stored in an oil vat of a fryer used for cooking fried food.

BACKGROUND ART

In order to maintain the quality of fried foods, it is necessary to appropriately manage the cooking oil (hereinafter, referred to as "frying oil") used for cooking (hereinafter, referred to as "deep-fry cooking") the fried foods. Conventionally, for determining when to dispose (change) the frying oil, there has been known a method of determining the degree of degradation of the frying oil (hereinafter, referred to as "degradation degree") based on indicators such as the smell and color of the frying oil which vary with time.

For example, as a degradation degree determination method based on the color of frying oil, a method in which a person in charge of determination (in many cases, a user of the frying oil) compares the color of the frying oil scooped up from an oil vat with a color sample that shows the gradual change in the color of cooking oil. However, such a determination method often depends on the subjectivity of the person in charge of determination.

Therefore, as a method of objectively determining the degradation degree of frying oil without depending on the subjectivity of a person in charge of determination, for example, Patent Literature 1 discloses a method of detecting the amount of bubbles formed on the surface of the frying oil during deep-fry cooking and using how much the detected intensity of illumination has varied as an indicator to detect the degradation degree of the quality of the frying oil.

CITATION LIST

Patent Literature

Patent Literature 1: JP-A-H08-182624

SUMMARY OF INVENTION

Technical Problem

However, in the method according to Patent Literature 1, due to the influence of the surrounding environment in which the surface of the frying oil is illuminated, the level of brightness of a light installed around the fryer affects the accuracy in the detection of the intensity of illumination. In order to prevent this influence, it is necessary to keep the intensity of illumination around the fryer at the one suitable for determination of the degradation degree. That is, in Patent Literature 1, adjustment of the brightness of the place where the fryer is installed in advance is necessary, which reduces the generality of the degradation degree determination based on the intensity of illumination of the surface of the frying oil.

In view of the above, an object of the present invention is to provide a cooking oil degradation degree determination device, a cooking oil degradation degree determination processing device, a cooking oil degradation degree determination method, and a fryer, which are capable of accurately determining the degradation degree of frying oil regardless of the environment around a fryer.

Solution to Problem

In order to achieve the object described above, the present invention provides a cooking oil degradation degree determination device for determining a degradation degree of a cooking oil used in deep-fry cooking for cooking a fried food, comprising: a fryer that includes an oil vat for storing the cooking oil therein and at least one color sample for displaying gradual change in a color of the cooking oil, the fryer being used for the deep-fry cooking of a food put into the oil vat; an imaging device that captures an oil surface image that is an image of a surface of the cooking oil; and a controller that executes degradation degree determination processing for determining the degradation degree of the cooking oil based on a captured image by the imaging device, the at least one color sample being arranged at a position included within an angle of view of the imaging device which is the same as an angle of view thereof for the oil surface image, and the controller being configured to: identify, from the captured image by the imaging device, the oil surface image and a color sample image that is an image of the at least one color sample; extract a color of the surface of the cooking oil from the oil surface image as identified and a plurality of colors displayed on the at least one color sample from the color sample image as identified, respectively; compare the color of the surface of the cooking oil as extracted with the plurality of colors of the at least one color sample as extracted, respectively, determine which of the plurality of colors of the at least one color sample the color of the surface of the cooking oil corresponds to; and determine the degradation degree of the cooking oil based on one of the colors of the at least one color sample which has been determined to correspond to the color of the surface of the cooking oil.

Advantageous Effects of Invention

According to the present invention, it is possible to accurately determine the degradation degree of frying oil regardless of an environment around a fryer. The problems, configurations, and advantageous effects other than those described above will be clarified by explanation of the embodiments below.

DESCRIPTION OF EMBODIMENTS

The cooking oil degradation degree determination device according to each embodiment of the present invention is a device for determining the degradation degree of cooking oil used for cooking fried foods such as fried chickens, croquettes, and french fries. In the following, cooking fried foods is referred to as "deep-fry cooking", and cooking oil used for deep-fry cooking is referred to as "frying oil".

(Arrangement in Cooking Area 1)

Firstly, an exemplary arrangement in a cooking area 1, which is assumed as an environment in which deep-fry cooking is performed, will be described with reference to FIG. 1.

Figure 1:
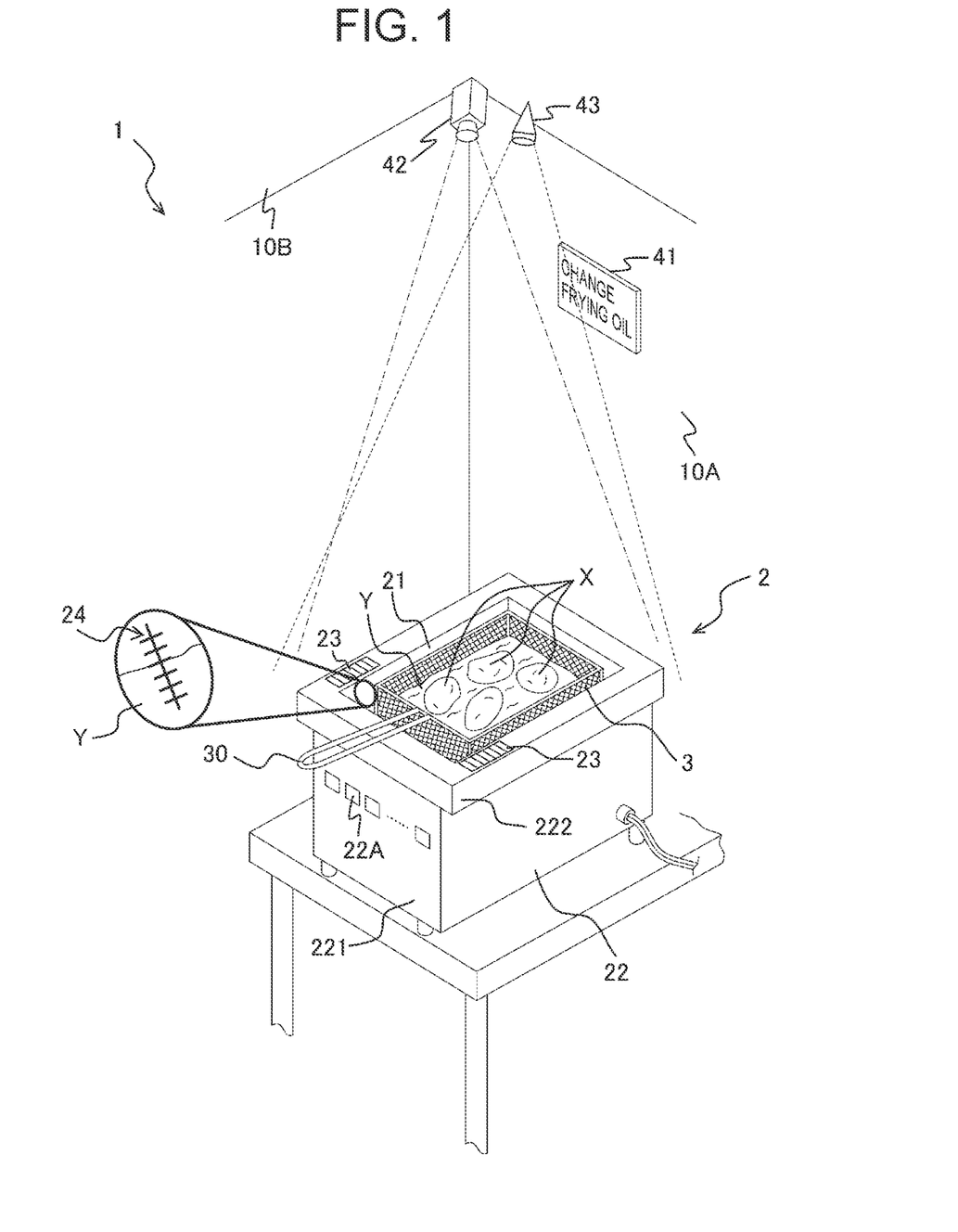
FIG. 1 illustrates an exemplary arrangement in a cooking area where deep-fry cooking is performed.

FIG. 1 illustrates an exemplary arrangement in the cooking area 1 where deep-fry cooking is performed.

The cooking area 1 is built in stores and shops such as convenience stores, supermarkets, and the like. In the cooking area 1, equipment, such as an electric fryer 2, for deep-fry cooking to produce a fried food X to be sold to customers is installed. The fryer 2 includes an oil vat 21 for holding frying oil Y therein which has a rectangular shape as viewed from above, and a housing 22 for accommodating the oil vat 21.

On an outer surface 221 of the housing 22, a plurality of switches 22A as a setting operation unit for setting the temperature of the frying oil Y and the details of the deep-fry cooking is provided for each type of the deep-fried food X. Furthermore, as illustrated in an enlarged view in FIG. 1, on a wall surface of the oil vat 21 corresponding to an inner wall surface of the housing 22, a scale 24 is provided to clearly indicate the positions in the depth direction of the oil vat 21. The scale 24 is provided for identifying the position of the surface of the frying oil Y stored in the oil vat 21, and used in measurement of the amount of oil. Specifically, an image of the scale 24 which has been captured together with an oil surface image captured (taken) by a video camera 42 which will be described later is used in determination of the height of the oil level of the frying oil Y. Accordingly, the scale 24 may be provided on any of the inner wall surfaces of the housing 22 as long as the amount of oil can be measured using the image captured by the video camera 42, and a position to which the scale 24 is to be provided is not limited as well.

For deep-fry cooking, firstly, a cook places the fried food X before deep-fried in a fry basket 3 having a handle 30, and then hooks the handle 30 on an upper edge portion 222 of the housing 22 so that the fried food X in the fry basket 3 is immersed in the frying oil Y that has heated at the temperature suitable for deep-fry cooking. At the same time or around the same time, the cook presses one of the switches 22A which corresponds to the type of the fried food X in cooking.

Subsequently, the fryer 2 identifies the switch 22A manipulated by the cook, and upon elapse of the deep-fry time associated with the manipulated switch 22A, notifies the cook of the finishing of deep-frying. At the same time, the fry basket 3 holding the fried food X automatically rises from the oil vat 21 so that the fried food X which has been immersed in the frying oil is pulled up. As a method of informing the finishing of deep-frying of the fried food X, for example, a method of outputting a buzzer sound from a speaker of the fryer 2 or a method of displaying the information on a monitor 41 installed on a wall 10A near the fryer 2 may be employed. That is, each of the speaker and the monitor 41 is one of the aspects of a notification device.

The cook who is aware of the finishing of deep-frying of the fried food X pulls up the fry basket 3 from the oil vat 21 to take the fried food X out from the fry basket 3. Note that pulling up the fry basket 3 out from the oil vat 21 may be automatically carried out by a drive mechanism which can be provided in the fryer 2.

In FIG. 1, the side where the cook stands, in other words, the side where the handle 30 of the fry basket 3 set in the oil vat 21 extends is referred to as the "front side" of the oil vat 21, and the opposite side is referred to as the "back side". A direction intersecting the width direction of the oil vat 21 is referred to as the "left and right direction".

The fryer 2 is provided with a color sample 23 showing the patterns of stages in which the color of the frying oil Y changes with time. The color sample 23 is, for example, a color scale according to color difference measurement such as the Gardner or the Lovibond, and corresponds to a sample used for visual evaluation of the degree of yellowness of the frying oil Y.

For configuring the color sample 23 illustrated in FIG. 1, among the eighteen different colors corresponding to the first to eighteenth yellowness values of the Gardner color scale, the seven colors having large values of yellowness (dark in the color) corresponding to the eleventh to seventeenth values are used to form rectangular region portions, and the rectangular region portions are arranged in order of color darkness. The color sample 23 may be arranged on any of the faces of the upper edge portion 222 of the housing 22, and moreover, as illustrated in FIG. 1, the multiple color samples 23 may be provided and arranged on the left and right sides of the oil vat 21, respectively. Note that, in the color sample 23, the number of colors to be displayed and the format for displaying the colors are not particularly limited as long as the color sample 23 shows at least the scales of the yellowness values necessary in the determination of the degradation degree of the frying oil Y.

Furthermore, regarding the color samples 23, the number and arrangement location thereof are not limited to those illustrated in FIG. 1, and for example, at the upper edge portion 222 of the housing 22, the front side and back side of the oil vat 21 may be provided therewith, respectively, all of the four sides surrounding the oil vat 21 may be provided therewith respectively, or any one side may be provided therewith. However, considering a risk that the color sample 23 gets dirty during deep-fry cooking due to the splashing frying oil Y, it is preferable to provide the color samples 23 at least on one side and the other side (opposed to the one side) of the oil vat 21, respectively.

In the cooking area 1, the video camera 42 as an imaging device for capturing an oil surface image which is an image of the surface of the frying oil Y in the oil vat 21 and a lighting device 43 arranged adjacent to the video camera 42 to simultaneously illuminate the surface of the frying oil Y and the color sample 23 (with the same intensity of illumination) are installed on a ceiling 10B above the oil vat 21.

The video camera 42 is fixed at an angle of view capable of continuously acquiring images of the surface of the frying oil Y in the oil vat 21, and is adjusted and installed with the focus being on the surface of the oil vat 21. In FIG. 1, the range of the adjusted angle of view of the video camera 42 is indicated by a dashed dotted line.

As illustrated in FIG. 1, the surface of the frying oil Y, the color samples 23, and the scale 24 are included inside the angle of view which is the range to be captured by the video camera 42. In other words, both the color samples 23 and the scale 24 are arranged at the positions included within the angle of view of the video camera 42 which is the same as the angle of view thereof for capturing the oil surface image (in FIG. 1, the color samples 23 are arranged on both left and right sides of the oil vat 21, and the scale 24 is arranged on the left inner surface of the housing 22).

Thus, the captured images by the video camera 42 include the oil surface image, a color sample image that is an image of the color samples 23, and a scale image that is an image of the scale 24. Comparing the scale image with the oil surface image enables identification of the position of the oil level of the frying oil Y and thus measurement of the amount of oil stored in the oil vat 21 based on the position of the oil level.

Specifically, the positions of the color samples 23 are preferably included in a focus range in which the color sample image captured by the video camera 42 is not blurred with the video camera 42 being installed so as to focus on the oil surface, and the same applies to the position of the scale 24.

Here, each of the monitor 41 and the video camera 42 is connected to a controller as a degradation degree determination processing device that carries out the degradation degree determination processing for determining the degradation degree of the frying oil Y. The controller determines the degradation degree of the frying oil Y based on the captured image data output from the video camera 42, and outputs a display signal indicating the determination result to the monitor 41. The monitor 41 displays the degradation degree of the frying oil Y, the information that the time to dispose the frying oil Y has arrived, and the like in accordance with the display signal output from the controller. A specific configuration of the controller will be described later for each embodiment.

Note that, in FIG. 1, the video camera 42 is installed on the ceiling 10B, however, the installation position of the video camera 42 is not limited thereto. The video camera 42 may be attached to, for example, the wall 10A as long as it is installed above the oil vat 21 with being held at a position capable of capturing the oil surface image. Furthermore, the imaging device does not necessarily have to be the video camera 42 for capturing a moving image, but may be, for example, a still camera for capturing a still image. In the case of using a still camera, it may be configured to automatically capture oil surface images intermittently. Still further, the video camera 42 does not necessarily have to capture the scale 24 together with the surface of the frying oil Y and the color samples 23. For capturing the scale 24, another imaging device that is different from the video camera 42 may be used.

In the same manner as the video camera 42, in FIG. 1, the lighting device 43 is attached to the ceiling 10B so as to be adjacent to the video camera 42, however, the installation position of the lighting device 43 is not limited thereto. The lighting device 43 may be attached to, for example, the wall 10A as long as it is installed above the oil vat 21 with being held so as to illuminate the surface of the frying oil Y and the color sample 23 with the same intensity of illumination, that is, held allowing the surface of the frying oil Y and the color sample 23 to be included within the broken line in FIG. 1. Furthermore, the monitor 41 also does not necessarily have to be attached to the wall 10A, and the arrangement location of the monitor 41 can be appropriately changed depending on the layout of the cooking area 1.

In the cooking area 1, deep-fry cooking using the fryer 2 is performed, and also the degradation degree of the frying oil Y can be determined by the cooking oil degradation degree determination device including the fryer 2 to which the color sample 23 is attached, the video camera 42 that captures an image of the surface of the frying oil Y stored in the oil vat 21 and an image of the color sample 23 at the same angle of view, and a controller 5 that carries out the degradation degree determination processing of the frying oil Y.

First Embodiment

The controller 5 according to the first embodiment of the present invention will be described with reference to FIG. 2 to FIG. 4.

(Configuration of Controller 5)

Firstly, the configuration of the controller 5 will be described with reference to FIG. 2 and FIG. 3.

Figure 2:
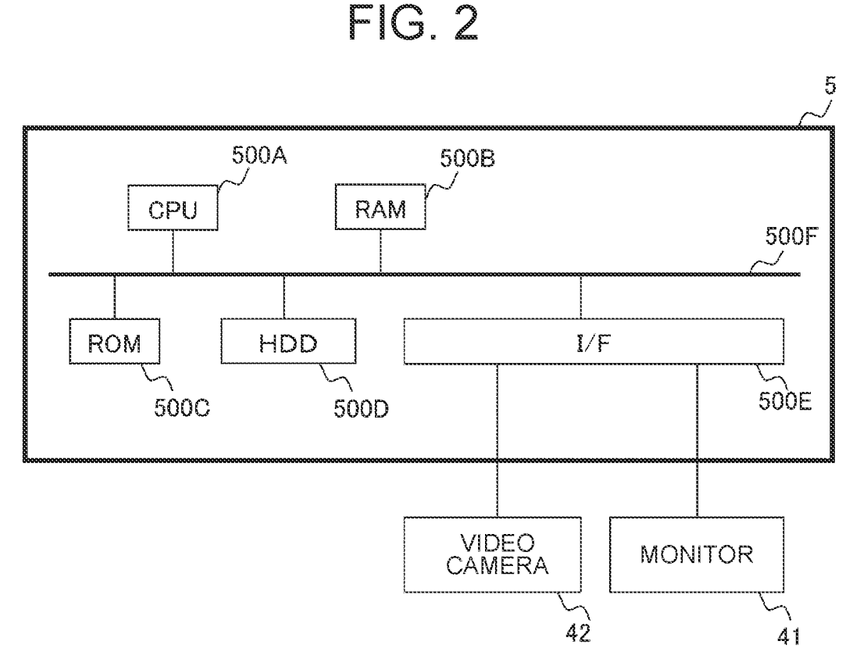
FIG. 2 is a configuration diagram illustrating an exemplary hardware configuration of a controller according to a first embodiment.

FIG. 2 is a configuration diagram illustrating an exemplary hardware configuration of the controller 5 according to the first embodiment. FIG. 3 is a functional block diagram illustrating functions of the controller 5 according to the first embodiment.

The controller 5 has a function of receiving, as input data, from the video camera 42 directly or indirectly via an external storage medium or further from a remote location through a communication line, a captured image including an oil surface image that is an image of the surface of the frying oil Y and a color sample image that is an image of the color sample 23, and a function of outputting, as output data, a determination result of the degradation degree of the frying oil Y. The controller 5 further has a function of notifying the outside such as a user of the determination result.

As illustrated in FIG. 2, the controller 5 includes a CPU (Central Processing Unit) 500A, a RAM (Random Access Memory) 500B, a ROM (Read Only Memory) 500C, an HDD (Hard Disk Drive) 500D, and an I/F (Interface) 500E as hardware resources. These are connected to each other via a common bus 500F.

The CPU 500A controls the whole operations of the controller 5. The RAM 500B is a volatile storage medium capable of reading and writing information at high speed, and is used, for example, as a work area where the CPU 500A executes the image information processing. The ROM 500C is a read-only nonvolatile storage medium, and retains programs such as a firmware.

The HDD 500D is a nonvolatile storage medium capable of reading and writing information and has a large storage capacity. The HDD 500D retains an OS (Operating System), control programs and application programs for executing various kinds of information processing which will be described later, and the like. Note that the HDD 500D may be substituted by a device which realizes functions of storing and managing information as a nonvolatile storage medium regardless of the type of device, and for example, such a device may be an SSD (Solid State Drive).

The I/F 500E is an interface for connection with a communication network, to which the video camera 42 that captures an image including an oil surface image and a color sample image, the monitor 41 that displays a user interface, and the like are connected.

The controller 5 having the hardware configuration described above is an information processing device that realizes, by an arithmetic function provided in the CPU 500A, processing functions of the control programs stored in the ROM 500C, the control programs and application programs loaded from a storage medium such as the HDD 500D into the RAM 500B. The information processing described above is executed, thereby configuring a software control unit including various functional modules of each of the controller 5. Combination of the software control unit configured as described above and the hardware resources including the configurations as described above configures the functional blocks that realize the functions of the controller 5.

Note that, in the present embodiment, the controller 5 is described as a computer composed of a combination of software and hardware, however, the present invention is not limited thereto. As one of the examples of configurations of other computers, an integrated circuit for implementing functions of a control program executed by the fryer 2 may be used.

Figure 3:
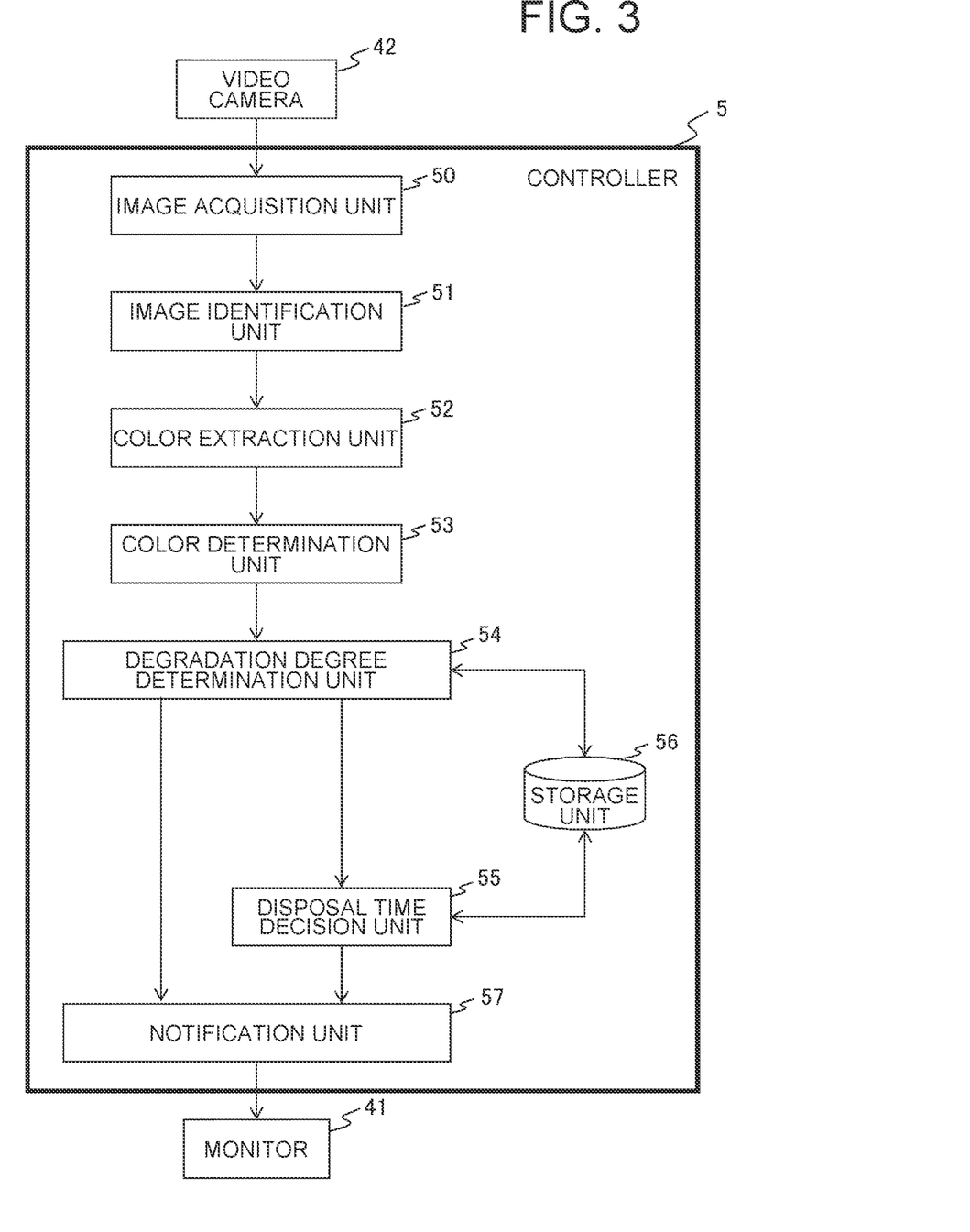
FIG. 3 is a functional block diagram illustrating functions of the controller according to the first embodiment.

As illustrated in FIG. 3, the controller 5 includes an image acquisition unit 50, an image identification unit 51, a color extraction unit 52, a color determination unit 53, a degradation degree determination unit 54, a disposal time decision unit 55, a storage unit 56, and a notification unit 57.

The image acquisition unit 50 acquires the captured image by the video camera 42, in other words, image data including an oil surface image and a color sample image (hereinafter, simply referred to as "captured image data"). For example, upon receiving a motion video of the fry basket 3, the image acquisition unit 50 separates the frames making up the input motion video into each of the frames (for example, in the case of a motion video at 30 fps, an image for every 1/30 second), and acquires the frames as captured image data, respectively. Upon receiving still images of the fry basket 3, the image acquisition unit 50 acquires, as captured image data, the input still images per se.

The image identification unit 51 identifies the oil surface image and the color sample image from the captured image data acquired by the image acquisition unit 50. Specifically, the image identification unit 51 extracts the outline of the fry basket 3 from the captured image data acquired by the image acquisition unit 50, and acquires only the inside of the extracted outline as the oil surface image. Furthermore, the image identification unit 51 extracts the outer edge of the color sample 23 from the captured image data acquired by the image acquisition unit 50, and acquires the color sample image from the image inside the extracted outer edge.

The image identification unit 51 further identifies the oil surface image and the scale image from the captured image data acquired by the image acquisition unit 50. The scale image identified by the image identification unit 51 is used as measurement data for calculating the amount of oil in the oil vat 21, and also is output to, for example, the monitor 41. That is, the measurement data is also used as data for displaying the amount of oil on the monitor 41.

The color extraction unit 52 uses the oil surface image identified by the image identification unit 51 to calculate RGB values of the picture elements (pixels) making up the oil surface image. Then, the color extraction unit 52 calculates an average value of the RGB values of the picture elements and uses the average value as an RGB value of the surface of the frying oil Y captured at a certain timing. Furthermore, the color extraction unit 52 uses the color sample image identified by the image identification unit 51 to calculate RGB values making up each of a plurality of different colors (seven colors corresponding to the eleventh to seventeenth yellowness values of the Gardner color scale) displayed on the color sample 23. That is, the color extraction unit 52 calculates an average value of the RGB values of the picture elements making up the image of each of the rectangular region portions included in the color sample 23 as an RGB value of each of these regions. Thus, the color extraction unit 52 extracts the plurality of (seven) RGB values displayed on the color sample 23, and also extracts the RGB value of the oil surface image captured simultaneously with the color sample image.

In order to extract the color of the surface of the frying oil Y with higher accuracy, the color extraction unit 52 may extract the RGB values of picture elements making up the surface image of a portion corresponding to a small dish attached to the fry basket 3 within the oil surface image. For example, a white small shallow dish is attached to the upper edge of the fry basket 3. The fry basket 3 rises after finishing of deep-frying of the fried food X, which causes a portion of the frying oil Y in the oil vat 21 to be scooped into the small dish. The frying oil Y filled in the small shallow dish is less in the depth than the frying oil Y in the deep oil vat 21, and thus the color of the frying oil Y in the small shallow dish appears clear. More specifically, as the frying oil Y in the deep oil vat 21, in other words, the frying oil Y that is deep degrades and the color thereof gets darker, the RGB value of the oil surface image has reached the peak, which causes the change in the color of the frying oil Y hardly to be seen. On the other hand, even if the frying oil Y filled in the small shallow dish, in other words, the frying oil Y that is shallow degrades and the color thereof gets darker, the color of the frying oil Y can be accurately determined based on a numerical value of the RGB value of the surface image of the portion filled in the small dish. Note that a method of analyzing the color of the surface of the frying oil Y and the plurality of different colors displayed on the color sample 23 is not necessarily limited to the method based on RGB values, and for example, it may be a method of analyzing a wavelength of a still image or a moving image captured by the video camera 42.

The color determination unit 53 compares the RGB value of the surface of the frying oil Y extracted by the color extraction unit 52 with the plurality of RGB values of the color sample 23 to determine which of the plurality of different colors of the color sample 23 the color of the surface of the frying oil Y corresponds to. In comparison of the RGB value of the surface of the frying oil Y with the plurality of RGB values of the color sample 23, the RGB value of the surface of the frying oil Y does not have to perfectly match any of the plurality of RGB values of the color sample 23, and the color determination unit 53 may use, as the determination result, the color of the color sample 23 having the RGB value that is the closest to the RGB value of the surface of the frying oil Y.

The degradation degree determination unit 54 determines the degradation degree of the frying oil Y based on the color of the color sample 23 determined by the color determination unit 53 as corresponding to the color of the surface of the frying oil Y. For example, when the color of the surface of the frying oil Y falls within the color corresponding to the eleventh yellowness value of the Gardner color scale in the color sample 23, the degradation degree determination unit 54 determines that the degradation degree of the frying oil Y is 50%, and when the color of the surface of the frying oil Y falls within the color corresponding to seventeenth yellowness value of the Gardner color scale in the color sample 23, the degradation degree determination unit 54 determines that the degradation degree of the frying oil Y is 100%.

Each relation between the Gardner color scale yellowness value and the degradation degree (%) of the frying oil Y is stored in advance in the storage unit 56, and can be appropriately changed in accordance with the purpose of use of the frying oil Y and the request of the cook. For example, the degradation degree of the color corresponding to the eleventh yellowness value of the Gardner color scale is not necessarily set to 50% as in the example describe above, and it may be set to 40%, 65%, or the like.

Furthermore, when the amount of the frying oil Y in the oil vat 21 changes due to supply or mixing of the oil, the color of the frying oil Y appears differently (specifically, the color of the frying oil Y appears darker as the amount of oil increases), and accordingly, the relation described above may be corrected in accordance with the amount of oil (for example, for a large amount of oil, setting the color corresponding to the sixteenth yellowness value of the Gardner color scale value to 100% degradation degree, and for a small amount of oil, setting the color corresponding to the thirteenth yellowness value of the Gardner color scale to 100% degradation degree).

Specifically, the controller 5 firstly stores the relation between the number of graduations of the scale 24 and the amount of the frying oil Y in the storage unit 56 in advance as oil amount data. Subsequently, based on the scale image captured by the video camera 42, the controller 5 detects the number of graduations above the oil level of the frying oil Y. Based on the detected number of graduations and the oil amount data stored in the storage unit 56, the controller 5 measures the current amount of the frying oil Y. Then, the controller 5 corrects the relation between the Gardner color scale yellowness value and the degradation degree of the frying oil Y stored in the storage unit 56 in accordance with the measured amount of oil.

The disposal time decision unit 55 determines whether the frying oil Y needs to be changed, that is, whether the disposal time of the frying oil Y has arrived, based on the degradation degree of the frying oil Y determined by the degradation degree determination unit 54. Each relation between the degradation degree (%) of the frying oil Y and the disposal time is stored in advance in the storage unit 56, for example, such that the disposal time is determined to have been reached at the degradation degree of 100%, or at the degradation degree of 85%.

The notification unit 57 outputs, to the monitor 41, a display signal indicating the degradation degree of the frying oil Y determined by the degradation degree determination unit 54. The monitor 41 displays, for example, "current degradation degree of frying oil Y is 00%". Furthermore, when the disposal time decision unit 55 determines that the disposal time of the frying oil Y has been reached, the notification unit 57 outputs, to the monitor 41, a display signal indicating to that effect. The monitor 41 displays, for example, "change frying oil Y".

As described above, the controller 5 compares the color of the surface of the frying oil Y with the plurality of colors of the color sample 23 based on the oil surface image and the color sample image included in the captured image by the video camera 42 to determine the degradation degree of the frying oil. This enables accurate determination of the degradation degree of the frying oil Y regardless of the environment around the fryer 2.

Furthermore, within the angle of view of the video camera 42 which is the same as the angle of view thereof for the oil surface image, the color sample 23 is arranged at a position included in the focus range in the oil surface image, which can cause, in comparison of the color of the surface of the frying oil Y with the plurality of colors of the color sample 23, the imaging condition for the oil surface image to be matched with that for the color sample image. This can further improve the accuracy in determination of the degradation degree of the frying oil Y. In addition, simultaneously illuminating the surface of the frying oil Y and the color sample 23 using the lighting device 43 enables the intensity of illumination of the surroundings thereof to be common. This can eliminate the problem that the determination is influenced by the brightness of the surroundings of the fryer 2.

(Processing in Controller 5)

Next, a specific flow of the processing executed in the controller 5 will be described with reference to FIG. 4.

Figure 4:
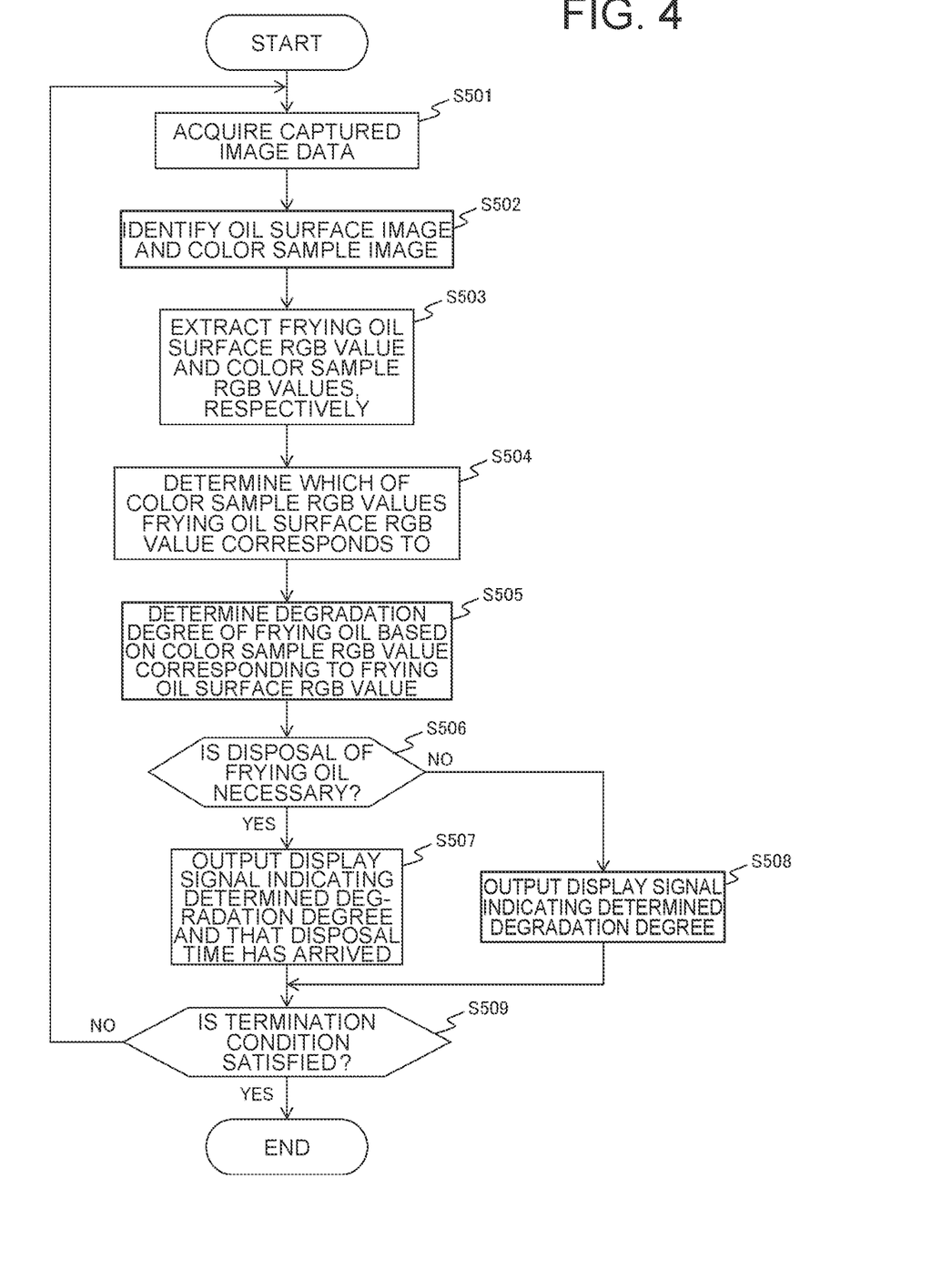
FIG. 4 illustrates a flowchart of processing executed by the controller according to the first embodiment.

FIG. 4 illustrates a flowchart of the processing executed by the controller 5 according to the first embodiment. Note that the processing described below is assumed to be executed repeatedly at predetermined time intervals while the controller 5 is working. The same applies to a second embodiment and a third embodiment.

First, the image acquisition unit 50 acquires, as the captured image data, the image captured by the video camera 42 in an imaging step (step S501). Next, the image identification unit 51 identifies the oil surface image and the color sample image from the captured image data acquired in step S501 (step S502; image identifying step).

Next, the color extraction unit 52 extracts, from the oil surface image identified in step S502, an RGB value of the surface of the frying oil Y (average value of the RGB values of the pixels making up the oil surface image) and a plurality of RGB values (average values of the RGB values of the pixels making up the colors corresponding to the yellowness values of the Gardner color scale, respectively) displayed on the color sample 23 from the color sample image identified in step S502, respectively (step S503; color extracting step). Subsequently, the color determination unit 53 compares the RGB value of the surface of the frying oil Y extracted in step S503 with the plurality of RGB values of the color sample 23, respectively, to determine which of the plurality of RGB values of the color sample 23 the RGB value of the surface of the frying oil Y corresponds to (step S504; color determining step).

Next, the degradation degree determination unit 54 determines the degradation degree of the frying oil Y based on the RGB value of the color sample 23, which has been determined to correspond to the RGB value of the surface of the frying oil Y in step S504 (step S505; degradation degree determining step). Subsequently, the disposal time decision unit 55 determines whether the frying oil Y needs to be disposed based on the degradation degree of the frying oil Y determined in step S505 (step S506; disposal determining step).

When it is determined in step S506 that the frying oil Y needs to be disposed (step S506/YES), the notification unit 57 outputs, to the monitor 41, a display signal indicating the degradation degree of the frying oil Y determined in step S505 and that the disposal time of the frying oil Y has arrived (step S507).

On the other hand, when it is determined in step S506 that the frying oil Y does not have to be disposed yet (step S506/NO), the notification unit 57 outputs, to the monitor 41, a display signal indicating only the degradation degree of the frying oil Y determined in step S505 (step S508).

After executing the processes in steps S507 and S508, the controller 5 subsequently determines whether a termination condition has been satisfied (for example, turning off the flyer 2) for terminating the series of processes (step S509).

Upon determining that the termination condition has been satisfied, the controller 5 ends the processing (step S509/YES) while, upon determining that the termination condition has not satisfied, the controller returns to step S501 and repeats the processing (step S509/NO).

If having acquired the captured image data of a motion video in step S501, the controller 5 may separate the acquired motion video for every 1/30 second and execute the processes from steps S502 to S506 with respect to the image of each of the separated frames. That is, the controller 5 may execute step S507 or step S508 depending on the determination result in step S506 made for the image of each of the separated frames.

Furthermore, the controller 5 may execute the processes from steps S502 to S506 for the plurality of separated frames and execute the processes from steps S502 to S506 when the number of times that necessity of the disposal of the frying oil Y is determined in step S506 exceeds a predetermined threshold. In this case, the controller 5 may use the number of consecutive times that "YES" is determined in step S506 as an indicator.

Second Embodiment

Next, a controller 5A according to the second embodiment of the present invention will be described with reference to FIG. 5 and FIG. 6.

Figure 5:
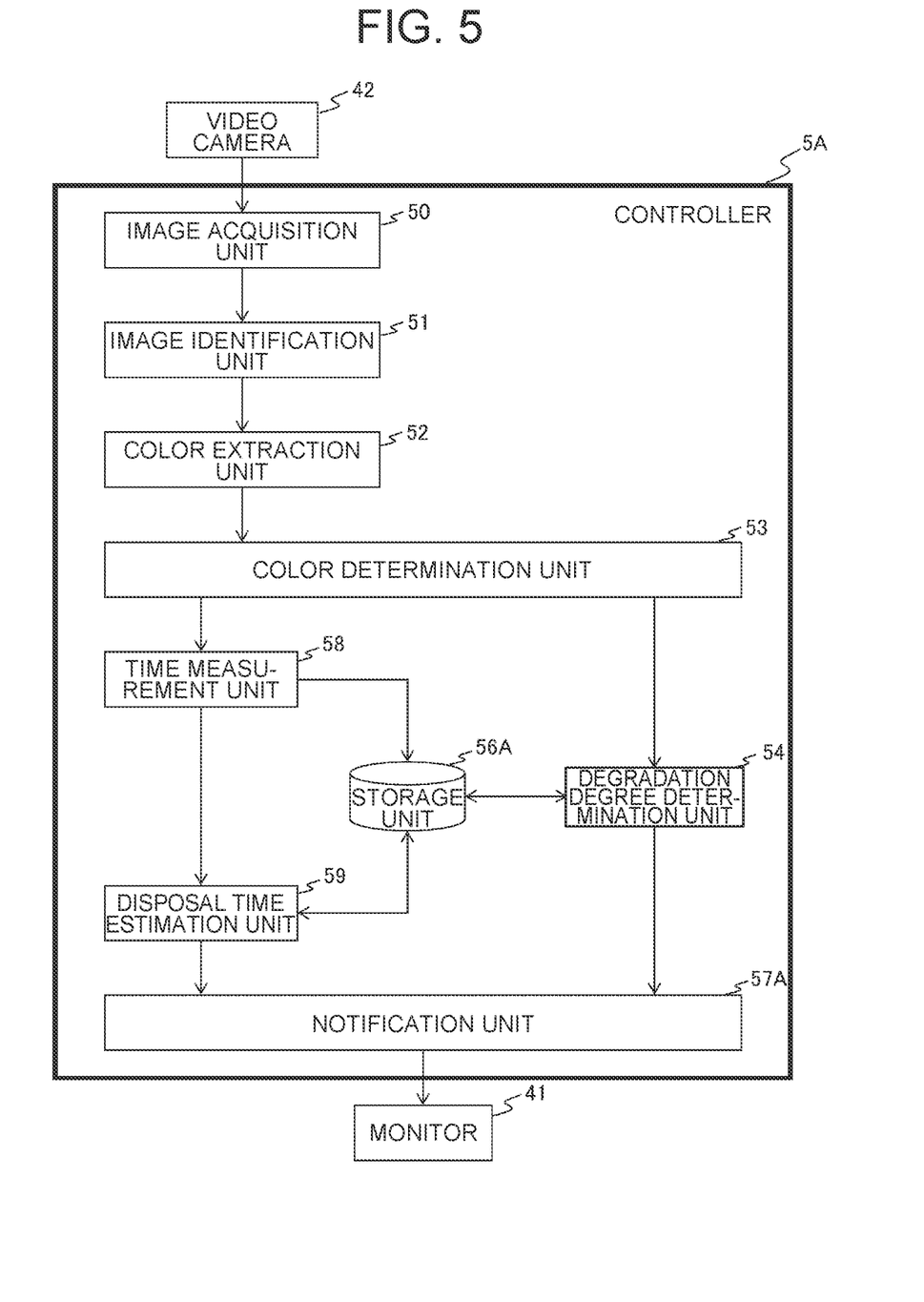
FIG. 5 is a functional block diagram illustrating functions of a controller according to a second embodiment.

FIG. 5 is a functional block diagram illustrating functions of the controller 5A according to the second embodiment. FIG. 6 illustrates a flowchart of the processing executed by the controller 5A according to the second embodiment. In FIG. 5 and FIG. 6, the elements common to those described for the controller 5 according to the first embodiment are provided with the same reference signs, and the repetitive description thereof will be omitted. The same applies to the third embodiment.

As illustrated in FIG. 5, the controller 5A according to the present embodiment includes the image acquisition unit 50, the image identification unit 51, the color extraction unit 52, the color determination unit 53, the degradation degree determination unit 54, a time measurement unit 58, a disposal time estimation unit 59, a storage unit 56A, and a notification unit 57A.

Figure 6:
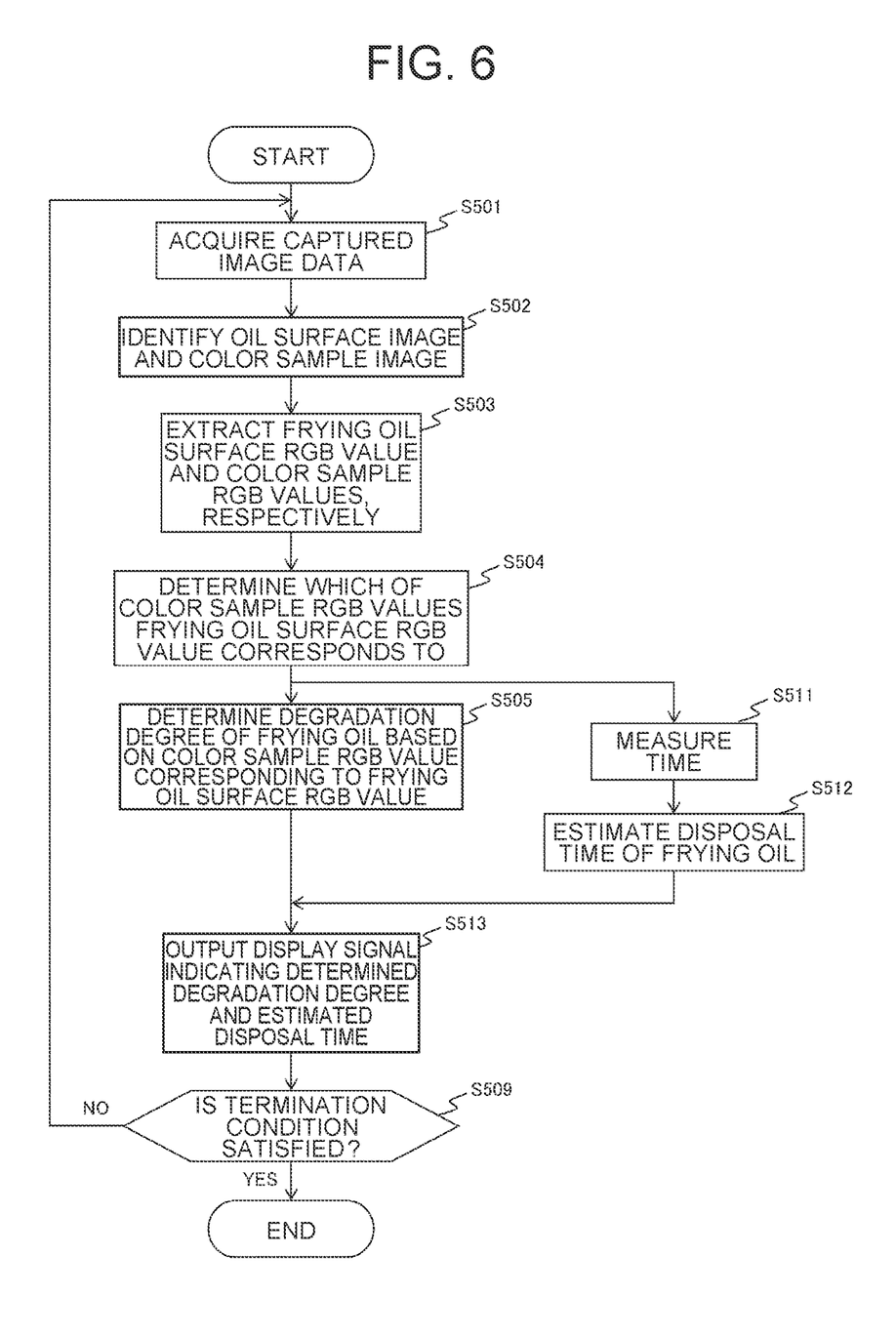
FIG. 6 illustrates a flowchart of processing executed by the controller according to the second embodiment.

As illustrated in FIG. 6, the processes from steps S501 to S504 executed in the controller 5A are the same as those from steps S501 to S504 executed in the controller 5 according to the first embodiment.

In the controller 5A, when it is determined in step S504 that the RGB value of the surface of the frying oil Y corresponds to any RGB value among the plurality of RGB values of the color sample 23, the processing proceeds to step S505 and also the time measurement unit 58 starts time measurement (step S511). The time measurement unit 58 measures the time in which the color of the color sample 23 determined by the color determination unit 53 as corresponding to the color of the surface of the frying oil Y changes, in other words, the time in which the yellowness value changes from the eleventh, twelfth, thirteenth . . . in the Gardner color scale.

Then, the disposal time estimation unit 59 estimates the disposal time of the frying oil Y based on the time (time change) measured by the time measurement unit 58 (step S512; disposal estimating step). Each relation between the time of change in the color of the color sample 23 measured by the time measurement unit 58 and the time until the disposal time of the frying oil Y has been reached is stored in advance in the storage unit 56A.

Subsequently, the notification unit 57A outputs, to the monitor 41, a display signal indicating the degradation degree of the frying oil Y determined in step S505 and the estimated disposal time of the frying oil Y estimated in step S512 (step S513). Upon satisfaction of the termination condition (step S509/YES), the controller 5A ends the processing. The monitor 41 displays, for example, "estimated disposal time of frying oil Y is 00 hours later".

As described above, the controller 5A according to the present embodiment not only determines the degradation degree of the frying oil Y but also estimates the disposal time. This enables a cook, a person taking charge of the fryer 2, and the like to be notified with the timing for changing the frying oil Y in advance.

Third Embodiment

Next, a controller 6 according to the third embodiment of the present invention will be described with reference to FIG. 7 and FIG. 8.

Figure 7:
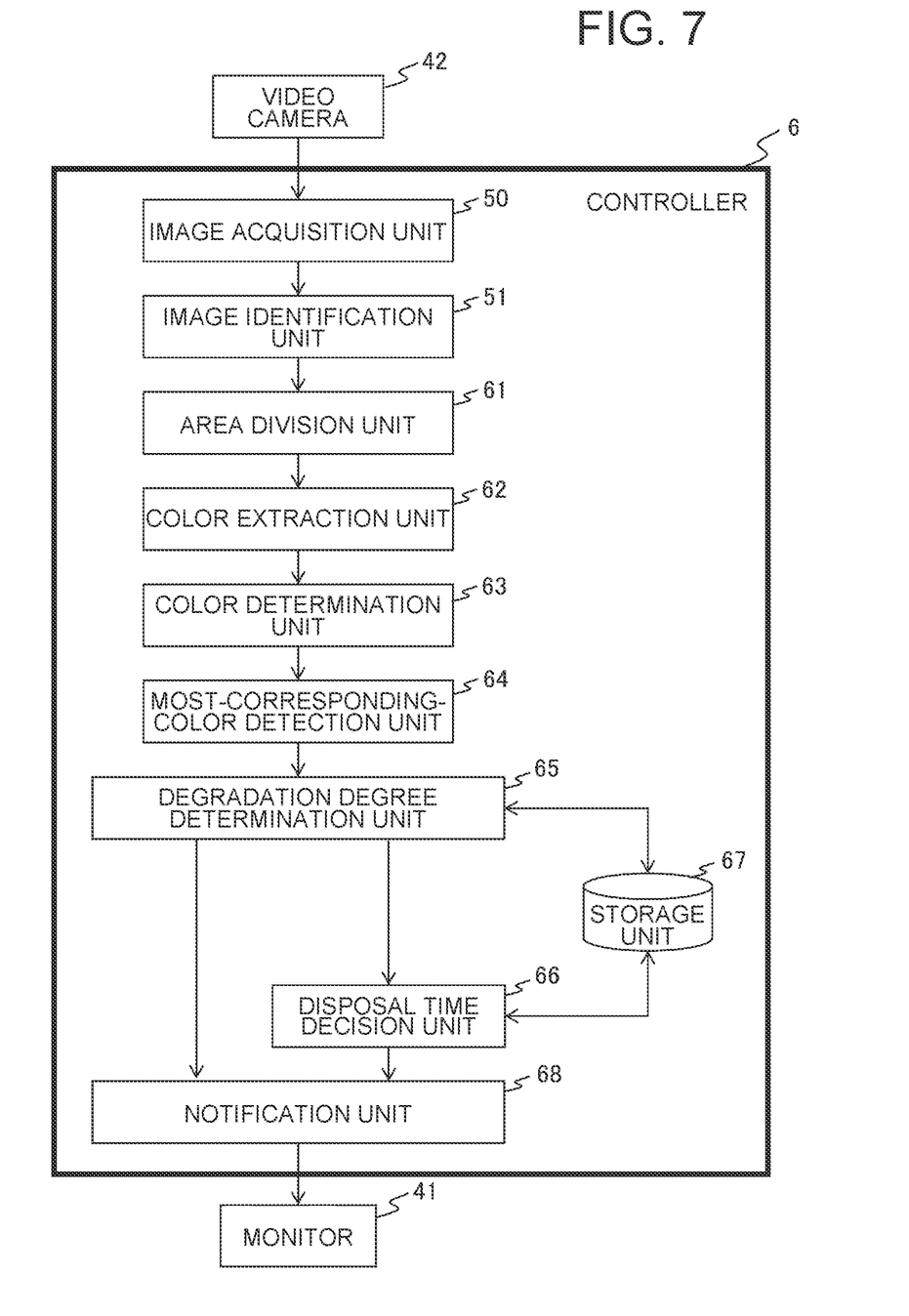
FIG. 7 is a functional block diagram illustrating functions of a controller according to a third embodiment.

FIG. 7 is a functional block diagram illustrating functions of the controller 6 according to the third embodiment. FIG. 8 illustrates a flowchart of the processing executed by the controller 6 according to the third embodiment.

As illustrated in FIG. 7, the controller 6 according to the present embodiment includes the image acquisition unit 50, the image identification unit 51, an area division unit 61, a color extraction unit 62, a color determination unit 63, a most-corresponding-color detection unit 64, a degradation degree determination unit 65, a disposal time decision unit 66, a storage unit 67, and a notification unit 68.

The area division unit 61 divides the oil surface image identified from the captured image data acquired by the image acquisition unit 50 into two-dimensional areas to acquire a plurality of oil surface area images. Then, the area division unit 61 passes each of the plurality of oil surface area images to the color extraction unit 62.

The color extraction unit 62 calculates, for each of the plurality of oil surface area images acquired by the area division unit 61, RGB values of the picture elements (pixels) making up the image, and uses an average value of the calculated RGB values as an RGB value of each of the oil surface area images. That is, a plurality of RGB values is acquired from the image of the surface of the frying oil Y captured at a certain timing. In the same manner as the color extraction unit 52 according to the first embodiment, the color extraction unit 62 extracts a plurality of (seven) RGB values displayed on the color sample 23 from the color sample image identified by the image identification unit 51.

The color determination unit 63 compares the RGB value of each of the oil surface area images as the RGB value of the surface of the frying oil Y extracted by the color extraction unit 62 with the plurality of RGB values of the color sample 23 to determine which of the plurality of different colors of the color sample 23 the color of each of the oil surface area images corresponds to. In comparison of the RGB value of the surface of the frying oil Y with the plurality of RGB values of the color sample 23, the RGB value of the surface of the frying oil Y does not have to perfectly match any of the plurality of RGB values of the color sample 23, and the color determination unit 63 may use, as the determination result, the color of the color sample 23 having the RGB value that is the closest to the RGB value of the surface of the frying oil Y.

The most-corresponding-color detection unit 64 detects the RGB value of the color sample 23, which has been determined by the color determination unit 63 to most often correspond to the RGB values of the oil surface area images. That is, the most-corresponding-color detection unit 64 detects the most-corresponding RGB value, in terms of the number of the oil surface images corresponding to each of the RGB values of the color sample 23.

Figure 8:
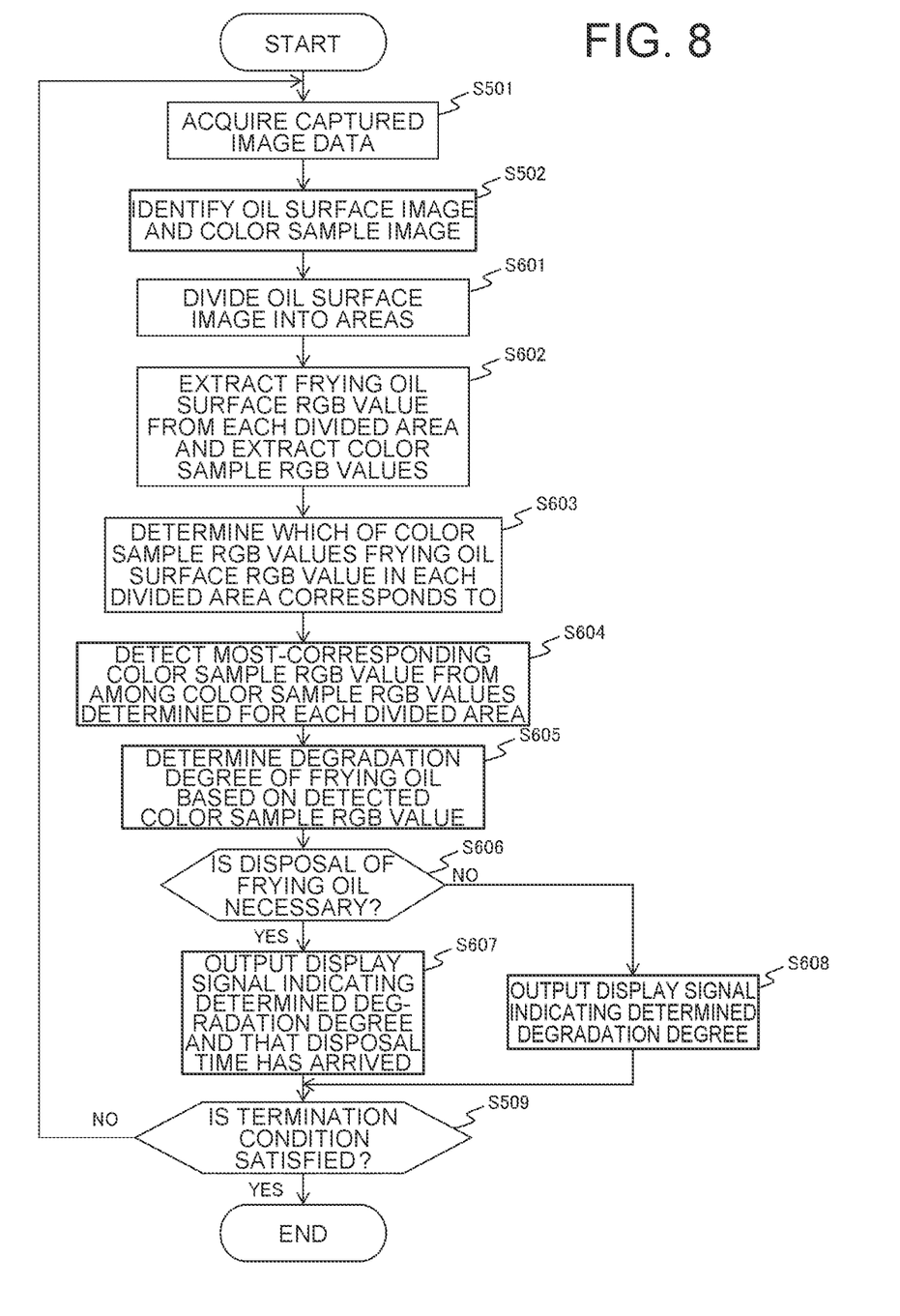
FIG. 8 illustrates a flowchart of processing executed by the controller according to the third embodiment.

As illustrated in FIG. 8, the processes from steps S501 to S502 executed in the controller 6 are the same as those from steps S501 to S502 executed in the controller 5 according to the first embodiment or in the controller 5A according to the second embodiment.

In the controller 6, when the oil surface image and the color sample image are identified from the captured image data in step S502, the area division unit 61 divides the oil surface image into a plurality of areas (step S601; area dividing step).

Next, the color extraction unit 62 extracts an average value of the RGB values in each of the areas (oil surface area images) divided in step S601, and also extracts the plurality of RGB values displayed on the color sample 23 from the color sample image identified in step S502 (step S602; color extracting step).

Next, the color determination unit 63 determines which of the plurality of RGB values of the color sample 23 extracted in step S602 the RGB value of each of the oil surface area images extracted in step S602 corresponds to (step S603; color determining step).

Then, the most-corresponding-color detection unit 64 detects, from among the RGB values of the color sample 23 which have been determined to correspond to the RGB value of the surface of the frying oil Y in each of the areas, the most-corresponding RGB value of the color sample 23 (step S604).

For example, suppose that, in the case where the oil surface image is divided into nine areas (first to ninth areas) in step S601, it is determined in step S603 that the RGB value of the surface of the frying oil Y in each of the first to fifth areas corresponds to the twelfth yellowness value of the Gardner color scale, the RGB value of the surface of the frying oil Y in each of the sixth and eighth areas corresponds to the seventeenth yellowness value of the Gardner color scale, the RGB value of the surface of the frying oil Y in the seventh region corresponds to the eleventh yellowness value, and the RGB value of the surface of the frying oil Y in the ninth region corresponds to the sixteenth yellowness value of the Gardner color scale. In this case, in step S604, the most-corresponding-color detection unit 64 detects, as the most-corresponding color, the twelfth yellowness value of the Gardner color scale which has been determined to correspond to the RGB values of the surface of the frying oil Y in the five areas (first to the fifth areas) which are the most in the number.

It is preferable that the RGB values of the plurality of oil surface area images are the same, since, by which is considered that the frying oil Y is in a uniform state. However, it is natural to consider that acquiring the oil surface images over time by the controller 6 to calculate an RGB value at every acquisition timing causes fluctuations in the color of the frying oil Y at each acquisition timing. Therefore, in the present embodiment, the controller 6 divides the surface of the frying oil Y into virtual areas to determine the color of the surface of the frying oil Y based on the majority of RGB values of the areas.

Subsequently, the degradation degree determination unit 65 determines the degradation degree of the frying oil Y based on the RGB value of the color sample 23 as the detected most-corresponding color in step S604 (step S605; degradation degree determining step). In the same manner as the first embodiment, each relation between the RGB value of the color sample 23 (Gardner color scale yellowness value) and the degradation degree (%) of the frying oil Y is stored in advance in the storage unit 67.

Next, the disposal time decision unit 66 determines whether the frying oil Y needs to be disposed based on the degradation degree of the frying oil Y determined in step S605 (step S606). In the same manner as the first embodiment, each relation between the degradation degree (%) of the frying oil Y and the disposal time is stored in advance in the storage unit 67.

When it is determined in step S606 that the frying oil Y needs to be disposed (step S606/YES), the notification unit 68 outputs, to the monitor 41, a display signal indicating the degradation degree determined in step S605 and that the disposal time of the frying oil Y has arrived (step S607). Upon satisfaction of the termination condition (step S509/YES), the controller 6 ends the processing.

On the other hand, when it is determined in step S606 that the frying oil Y does not have to be disposed yet (step S606/NO), the notification unit 68 outputs, to the monitor 41, a display signal indicating only the degradation degree of the frying oil Y determined in step S605 (step S608). Upon satisfaction of the termination condition (step S509/YES), the controller 6 ends the processing.

As described above, the controller 6 according to the present embodiment divides the oil surface image into a plurality of areas, and determine the degradation degree of the frying oil Y based on an RGB value of the color sample 23 to which an RGB value of the surface of the frying oil Y in each of the areas most corresponds among RGB values of the color sample 23. This enables the accurate determination of the degradation degree of the frying oil Y even if there are variations in the color of the surface of the frying oil Y. Note that the accuracy in the determination of the degradation degree of the frying oil Y improves as the oil surface image is divided more in the number.

Each of the controllers 5, 6 according to the first to third embodiments may be connected to the video camera 42 and the monitor 41 via a communication network so as to be operated remotely, or may be provided inside the housing of the video camera 42 and monitor 41. The communication network may be wired or wireless, and also is not limited to a particular communication method.

Herein, the present invention has been described with reference to the embodiments. The present invention is not limited to the embodiments described above, and various modifications may be made therein. For example, each of the embodiments is described in detail herein for the purpose of clarity and a concise description, and the present invention is not necessarily limited to those including all the features described above. Furthermore, some of the features according to a predetermined embodiment can be replaced with other features according to separate embodiments, and other features can be added to the configuration of a predetermined embodiment. Still further, some of the features can include other features of the separate embodiments, be deleted, and/or replaced.

REFERENCE SIGNS LIST

2: fryer
5: controller, cooking oil degradation degree determination device
21: oil vat
23: color sample
42: video camera (imaging device)

43: lighting device
51: image identification unit
52, 62: color extraction unit
53, 64: color determination unit
54, 65: degradation degree determination unit
Y: fry oil (cooking oil)

The invention claimed is:

1. A cooking oil degradation degree determination device for determining a degradation degree of a cooking oil used in deep-fry cooking for cooking a fried food, comprising:
   a fryer that includes an oil vat for storing the cooking oil therein and at least one color sample for displaying gradual change in a color of the cooking oil, the fryer being used for the deep-fry cooking of a food put into the oil vat;
   an imaging device that captures an oil surface image that is an image of a surface of the cooking oil; and
   a controller that executes degradation degree determination processing for determining the degradation degree of the cooking oil based on a captured image by the imaging device,
   the at least one color sample being arranged at a position included within an angle of view of the imaging device which is the same as an angle of view thereof for the oil surface image, and
   the controller being configured to:
      identify, from the captured image by the imaging device, the oil surface image and a color sample image that is an image of the at least one color sample;
      extract a color of the surface of the cooking oil from the oil surface image as identified and a plurality of colors displayed on the at least one color sample from the color sample image as identified, respectively;
      compare the color of the surface of the cooking oil as extracted with the plurality of colors of the at least one color sample as extracted, respectively;
      determine which of the plurality of colors of the at least one color sample the color of the surface of the cooking oil corresponds to; and
      determine the degradation degree of the cooking oil based on one of the colors of the at least one color sample which has been determined to correspond to the color of the surface of the cooking oil.

2. The cooking oil degradation degree determination device according to claim 1, wherein
   the position of the at least one color sample is included in a focus range of the imaging device in the oil surface image.

3. The cooking oil degradation degree determination device according to claim 1, wherein
   the oil vat is formed to have a rectangular shape as viewed from above,
   the at least one color sample comprises a plurality of color samples, and
   the plurality of color samples is arranged on at least one side of the oil vat and the other side opposite to the one side, respectively.

4. The cooking oil degradation degree determination device according to claim 1, further comprising a lighting device installed above the oil vat to illuminate the surface of the cooking oil and the at least one color sample with a same intensity of illumination.

5. The cooking oil degradation degree determination device according to claim 1, wherein
   the controller is configured to:
      divide the oil surface image as identified into a plurality of areas;
      extract an RGB value of the surface of the cooking oil from each of the plurality of areas as divided, and also extract a plurality of RGB values displayed on the at least one color sample from the color sample image as identified;
      determine which of the RGB values of the plurality of colors of the at least one color sample the RGB value of the surface of the cooking oil in each of the plurality of areas as extracted corresponds to;
      detect, from among the colors of the at least one color sample having the RGB values which have been determined to correspond to the RGB value of the surface of the cooking oil in each of the plurality of areas, one of the colors of the at least one color sample which has been most often determined, and
      determine the degradation degree of the cooking oil based on the one of the colors of the at least one color sample as detected.

6. The cooking oil degradation degree determination device according to claim 1, wherein
   the controller is configured to:
      measure a time in which the one of the colors of the at least one color sample, which has been determined to correspond to the color of the surface of the cooking oil, changes; and
      based on the time as measured, estimate a disposal time of the cooking oil.

7. A degradation degree determination processing device that executes degradation degree determination processing for determining a degradation degree of a cooking oil based on a captured image by an imaging device installed above an oil vat of a fryer used in deep-fry cooking for cooking a fried food to capture an oil surface image that is an image of a surface of the cooking oil stored in the oil vat, comprising:
   an image identification unit that identifies, from the captured image by the imaging device, the oil surface image and a color sample image that is an image of a color sample, the color sample being arranged so as to be included within an angle of view that is the same as an angle of view for the oil surface image and displaying gradual change in a color of the cooking oil;
   a color extraction unit that extracts a color of the surface of the cooking oil from the oil surface image identified by the image identification unit and a plurality of colors displayed on the color sample from the color sample image identified by the image identification unit;
   a color determination unit that compares the color of the surface of the cooking oil extracted by the color extraction unit with the plurality of colors of the color sample to determine which of the plurality of colors of the color sample the color of the surface of the cooking oil corresponds to; and
   a degradation degree determination unit that determines the degradation degree of the cooking oil based on one of the colors of the color sample which has been determined by the color determination unit to correspond to the color of the surface of the cooking oil.

* * * * *